(12) United States Patent
Kim et al.

(10) Patent No.: US 12,635,868 B2
(45) Date of Patent: **\*May 26, 2026**

(54) INTRAORAL SCANNER CALIBRATION DEVICE

(71) Applicant: OSSTEMIMPLANT CO., LTD., Seoul (KR)

(72) Inventors: Eun Joong Kim, Seoul (KR); Hyun Ho Choi, Seoul (KR); Ju Myung Hong, Seoul (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 206 days.

This patent is subject to a terminal disclaimer.

(21) Appl. No.: 18/578,204

(22) PCT Filed: May 17, 2022

(86) PCT No.: PCT/KR2022/007075
§ 371 (c)(1),
(2) Date: Jan. 10, 2024

(87) PCT Pub. No.: WO2023/287005
PCT Pub. Date: Jan. 19, 2023

(65) Prior Publication Data
US 2024/0374128 A1    Nov. 14, 2024

(30) Foreign Application Priority Data

Jul. 15, 2021    (KR) ........................ 10-2021-0092795

(51) Int. Cl.
    *A61B 1/24*      (2006.01)
    *A61B 1/00*      (2006.01)
    *A61B 5/00*      (2006.01)

(52) U.S. Cl.
    CPC ............ *A61B 1/24* (2013.01); *A61B 1/00194* (2022.02); *A61B 5/0062* (2013.01); *A61B 5/0088* (2013.01); *A61B 2560/0223* (2013.01)

(58) Field of Classification Search
    CPC ..... A61B 1/24; A61B 1/00194; A61B 5/0062; A61B 5/0088; A61B 2560/0223;
    (Continued)

(56) References Cited

U.S. PATENT DOCUMENTS 10,500,017 B2    12/2019  Lv et al.
10,758,317 B2     9/2020  Yuan et al.
(Continued)

FOREIGN PATENT DOCUMENTS

KR    10-2018-0126164 A    11/2018
KR    10-2018-0126177 A    11/2018
(Continued)

OTHER PUBLICATIONS

International Search Report for PCT/KR2022/007075 dated Sep. 16, 2022.
Written Opinion for PCT/KR2022/007075 dated Sep. 16, 2022.

*Primary Examiner* — Timothy R Newlin
(74) *Attorney, Agent, or Firm* — Sughrue Mion, PLLC

(57) ABSTRACT

An embodiment of the present disclosure provides an oral scanner calibration device including: a casing into which an oral scanner body is inserted; a reflector part disposed on a central axis of the oral scanner body and configured to reflect light irradiated from an optical device of the oral scanner body; a pattern plate part configured to face the optical device through the reflector part; a rotating part mechanically fastened to the reflector part and the pattern plate part; and a driving part configured to provide a driving force to the rotating part, wherein, in conjunction with rotation of the rotating part, the reflector part linearly moves relative to the
(Continued)

oral scanner body, and the pattern plate part rotates about an optical axis of the light reflected by the reflector part.

5 Claims, 6 Drawing Sheets

(58) Field of Classification Search
CPC ..... A61B 1/00057; A61B 5/00; A61C 9/0053; A61C 9/006
See application file for complete search history.

(56) References Cited

U.S. PATENT DOCUMENTS

| | | | |
|---|---|---|---|
| 2014/0255868 A1* | 9/2014 | Jesenko | A61C 9/0046 |
| | | | 433/32 |
| 2016/0367336 A1 | 12/2016 | Lv et al. | |
| 2017/0128173 A1 | 5/2017 | Berner et al. | |
| 2018/0028065 A1* | 2/2018 | Elbaz | G06F 16/9535 |
| 2018/0333232 A1* | 11/2018 | Lee | A61B 1/24 |
| 2019/0388194 A1* | 12/2019 | Atiya | G06T 7/80 |
| 2020/0085532 A1 | 3/2020 | Yuan et al. | |
| 2020/0205942 A1* | 7/2020 | Pesach | G06V 20/653 |
| 2021/0244502 A1* | 8/2021 | Farkash | A61B 5/0077 |
| 2022/0117493 A1* | 4/2022 | Tao | A61B 5/0088 |
| 2023/0320825 A1* | 10/2023 | Wissmann | A61C 9/006 |
| | | | 433/29 |
| 2024/0138680 A1* | 5/2024 | Lee | A61B 5/0062 |

FOREIGN PATENT DOCUMENTS

| | | | |
|---|---|---|---|
| KR | 10-2129383 B1 | 7/2020 | |
| KR | 10-2152921 B1 | 9/2020 | |

* cited by examiner

INTRAORAL SCANNER CALIBRATION DEVICE

This Application is a National Stage of International Application No. PCT/KR2022/007075 filed May 17, 2022, claiming priority based on Korean Patent Application No. 10-2021-0092795 filed Jul. 15, 2021, the entire disclosures of which are incorporated herein by reference.

TECHNICAL FIELD

The present disclosure relates to an oral scanner calibration device, and more particularly, to a device for calibrating an oral scanner by utilizing a pattern plate or the like to improve accuracy of the oral scanner.

BACKGROUND ART

In the process of producing a dental prosthesis, impression taking is an important process for producing an accurate prosthesis. Conventionally, an impression is taken using an impression material, and a prosthesis is produced based on a plaster model produced after the impression is taken, but there is a disadvantage that there is an error due to deformation of the impression material and the use of plaster.

Accordingly, oral structures such as teeth or gums are measured using an optical 3D imaging device using an optical 3D scanner, and a dental prosthesis is produced using a computer-aided design (CAD)/computer-aided manufacturing (CAM) system. In particular, in recent years, a stereo vision method using images obtained by two or more imaging devices has been applied to an oral scanner.

In the oral scanner using the stereo vision method, an image of one point of an oral cavity is captured by two or more imaging devices to obtain two or more pieces of image data, and 3D distance information is obtained based on the two or more pieces of image data, and thus calibration is frequently required for the oral scanner in order to obtain accurate 3D model data. For this reason, a calibration tool is typically provided in the form of a cradle as a separate accessory in the 3D oral scanner.

Meanwhile, obtaining an image of a pattern plate from various angles during calibration helps improve the accuracy of calibration, but a calibration cradle disclosed in Korean Patent Registration No. 10-2129383 is configured so that a pattern plate is rotated over eight stages, 90° each time, in a circumferential direction, and linear reciprocating motion occurs in conjunction therewith.

RELATED ART DOCUMENT (Patent Document 1) Korean Patent Registration No. 10-2129383 (Date of Notification: Jul. 2, 2020)

DISCLOSURE

Technical Problem

The present disclosure is directed to providing an oral scanner calibration device that can obtain an image of a pattern plate from various angles and depths even without manual operation by a user.

Technical Solution

One aspect of the present disclosure provides an oral scanner calibration device including: a casing into which an oral scanner body is inserted; a reflector part disposed on a central axis of the oral scanner body and configured to reflect light irradiated from an optical device of the oral scanner body; a pattern plate part configured to face the optical device through the reflector part; a rotating part mechanically fastened to the reflector part and the pattern plate part; and a driving part configured to provide a driving force to the rotating part, wherein, in conjunction with rotation of the rotating part, the reflector part linearly moves relative to the oral scanner body, and the pattern plate part rotates about an optical axis of the light reflected by the reflector part.

In one embodiment, the rotating part may include: a rotating shaft configured to be rotated by the driving part and extend in a longitudinal direction; a first rotating part positioned at the other end of the rotating shaft and configured to transmit the driving force to the pattern plate part; and a second rotating part positioned at one side of the rotating shaft and configured to transmit the driving force to the reflector part.

In one embodiment, the pattern plate part may include: a pattern plate; and a support part configured to be engaged with the first rotating part and support the pattern plate for the pattern plate to be inclined relative to the optical axis.

In one embodiment, the reflector part may include: a plurality of reflectors; and a support part configured to be rotatably coupled to the second rotating part and support the reflectors, and the support part may linearly move during rotation of the second rotating part.

In one embodiment, the reflectors may consist of a first reflector and a second reflector, the first reflector may be positioned to form a 45° angle with the central axis, the second reflector may be positioned to form a 45° angle with the optical axis, and a plane including the first reflector and a plane including the second reflector may be orthogonal to each other.

In one embodiment, the reflector part may be seated on a guide rail formed on the casing, and the rotating shaft and the support part may be mechanically fastened so that, during rotation of the rotating shaft, the reflector part linearly moves along the guide rail.

Advantageous Effects

According to one aspect of the present disclosure, in conjunction with rotation of a rotating part, a pattern plate part rotates in place about an optical axis of incident light, and a reflector part linearly moves relative to an oral scanner body. Accordingly, an image of the pattern plate part can be obtained from various angles and depths during calibration, and thus, accuracy of calibration can be improved.

Further, since the rotating part receives a driving force from a driving part, calibration can be performed even without manual operation by a user, and thus convenience in use can be improved, and the time taken for calibration can be reduced.

The advantageous effects of the present disclosure are not limited to the above-mentioned advantageous effect and should be understood as including all effects inferable from configurations described in the detailed description or claims of the present disclosure.

MODES OF THE INVENTION

Figure 1:
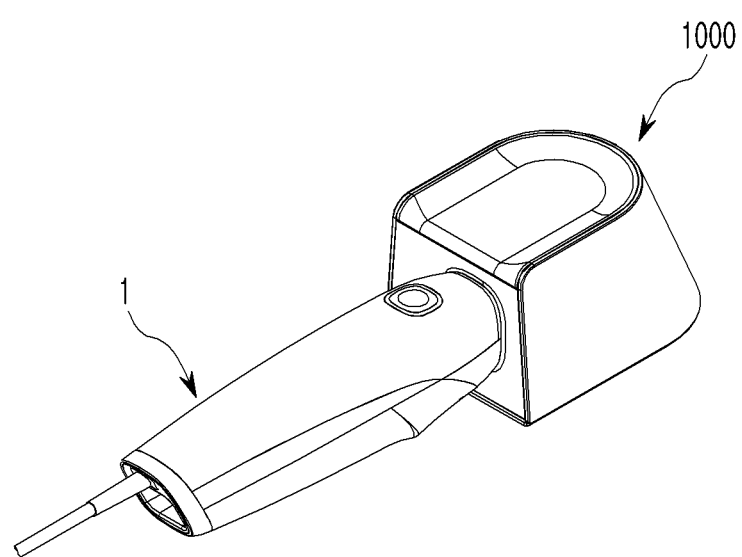
FIG. 1 is a perspective view of an oral scanner calibration device according to one embodiment of the present disclosure.

Hereinafter, the present disclosure will be described with reference to the accompanying drawings. However, the present disclosure may be implemented in various different forms and thus is not limited to the embodiments described herein. Also, in the drawings, parts irrelevant to the description have been omitted to clearly describe the present disclosure, and like parts are denoted by like reference numerals throughout the specification.

Throughout the specification, when a certain part is described as being "connected" to another part, this includes not only the case in which the certain part is "directly connected" to the other part, but also the case in which the certain part is "indirectly connected" to the other part with another member disposed therebetween. Also, when a certain part is described as "including" a certain element, the certain part may further include another element instead of excluding other elements unless particularly described otherwise.

Terms including ordinals such as "first" and "second" used herein may be used to describe various elements or steps, but the corresponding elements or steps should not be limited by ordinals. The terms including ordinals should be construed as only being used for the purpose of distinguishing one element or step from another element or step.

Hereinafter, embodiments of the present disclosure will be described in detail with reference to the accompanying drawings.

Figure 2:
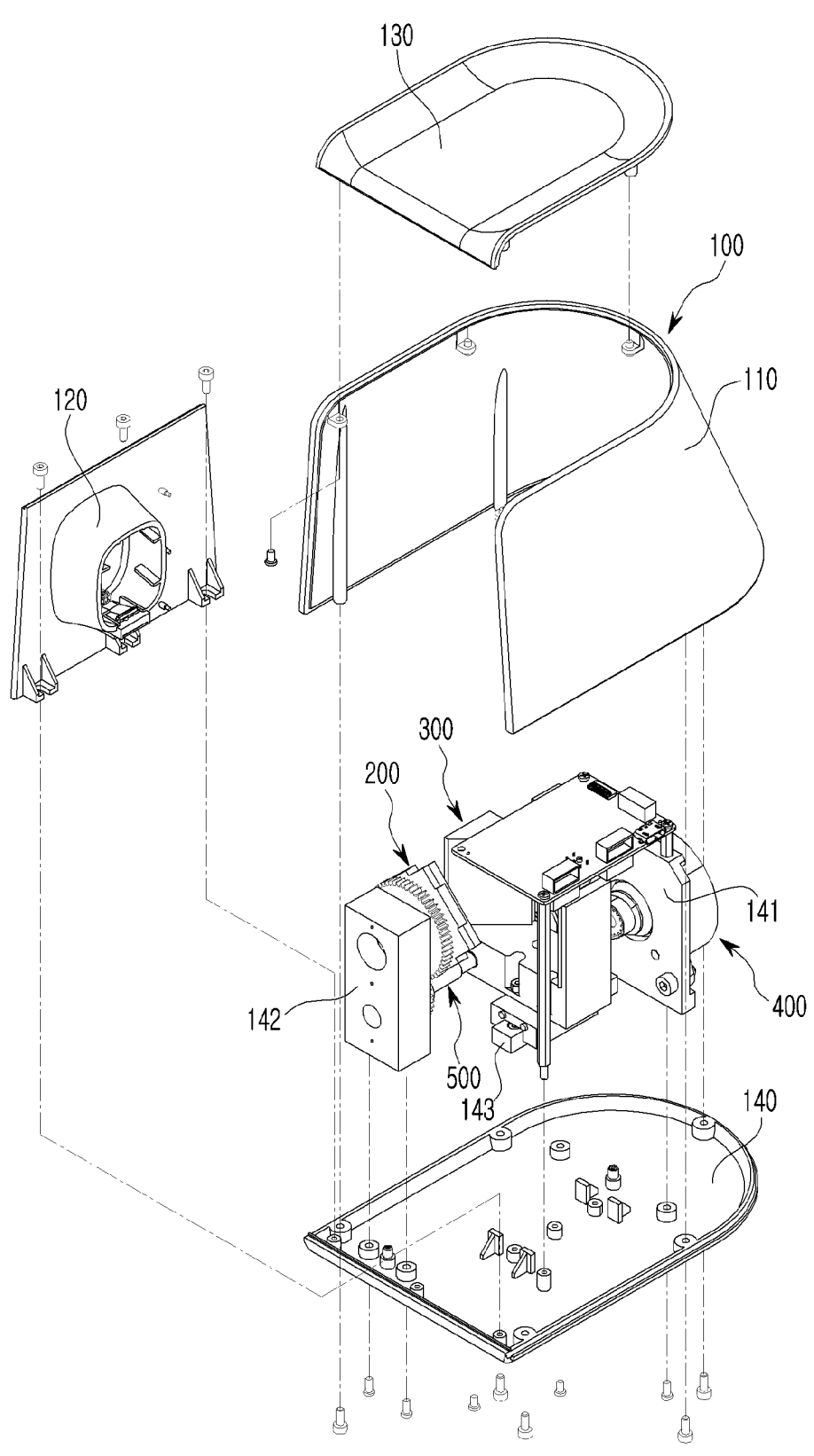
FIGS. 2 and 3 are exploded perspective views of the oral scanner calibration device according to one embodiment of the present disclosure.
Figure 3:
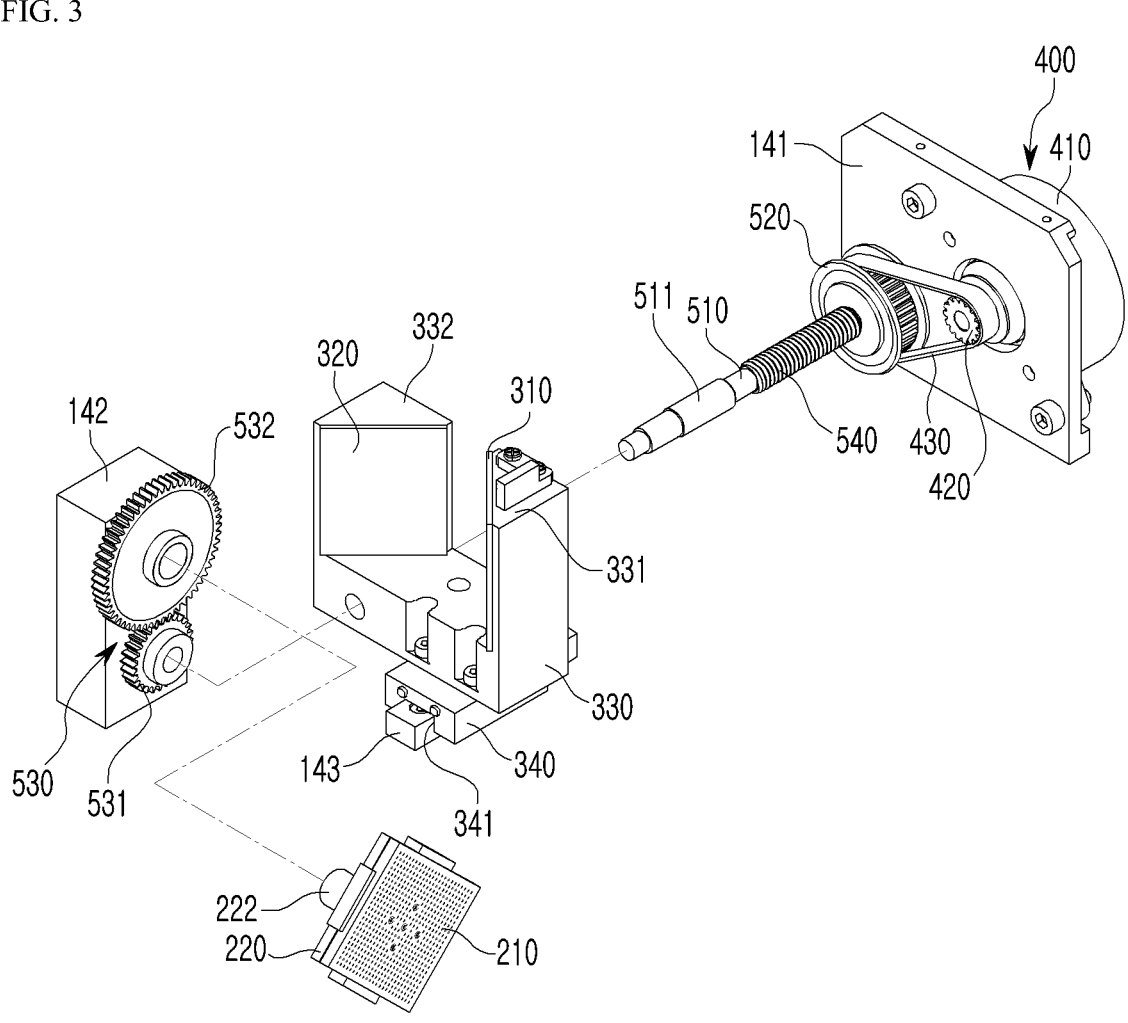
Figure 4:
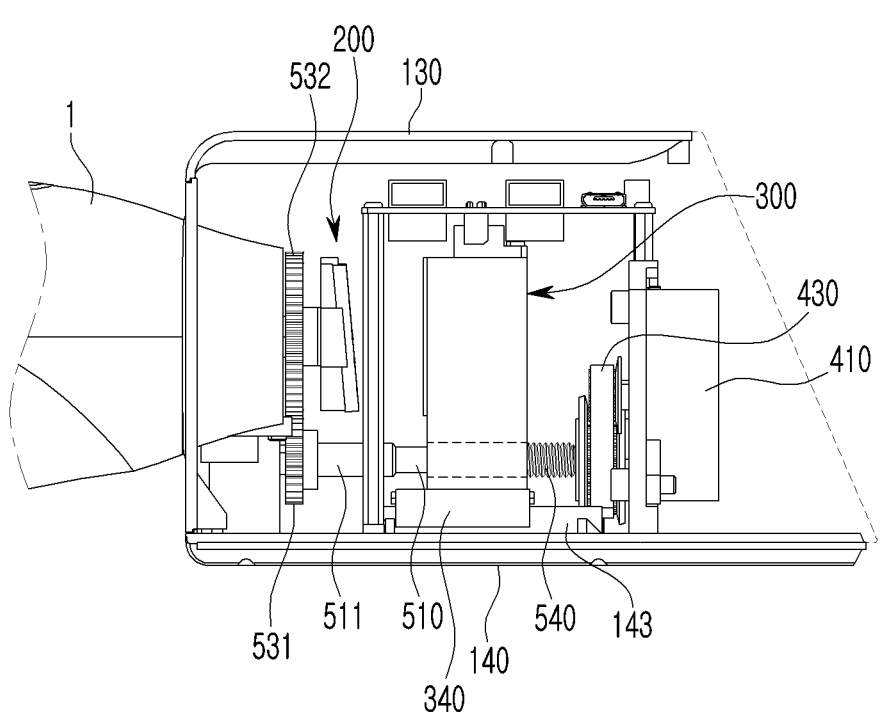
FIG. 4 is a lateral cross-sectional view of the oral scanner calibration device according to one embodiment of the present disclosure.
Figure 5:
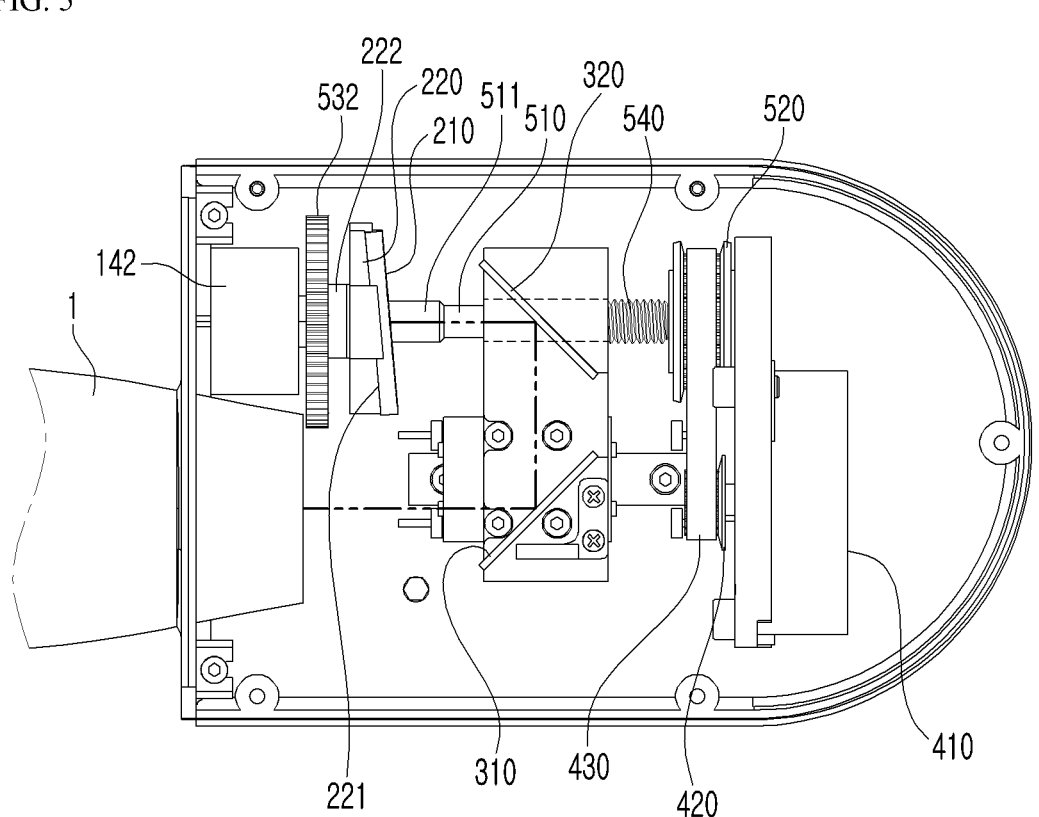
FIGS. 5 and 6 are cross-sectional views showing an operational process of the oral scanner calibration device according to one embodiment of the present disclosure.
Figure 6:
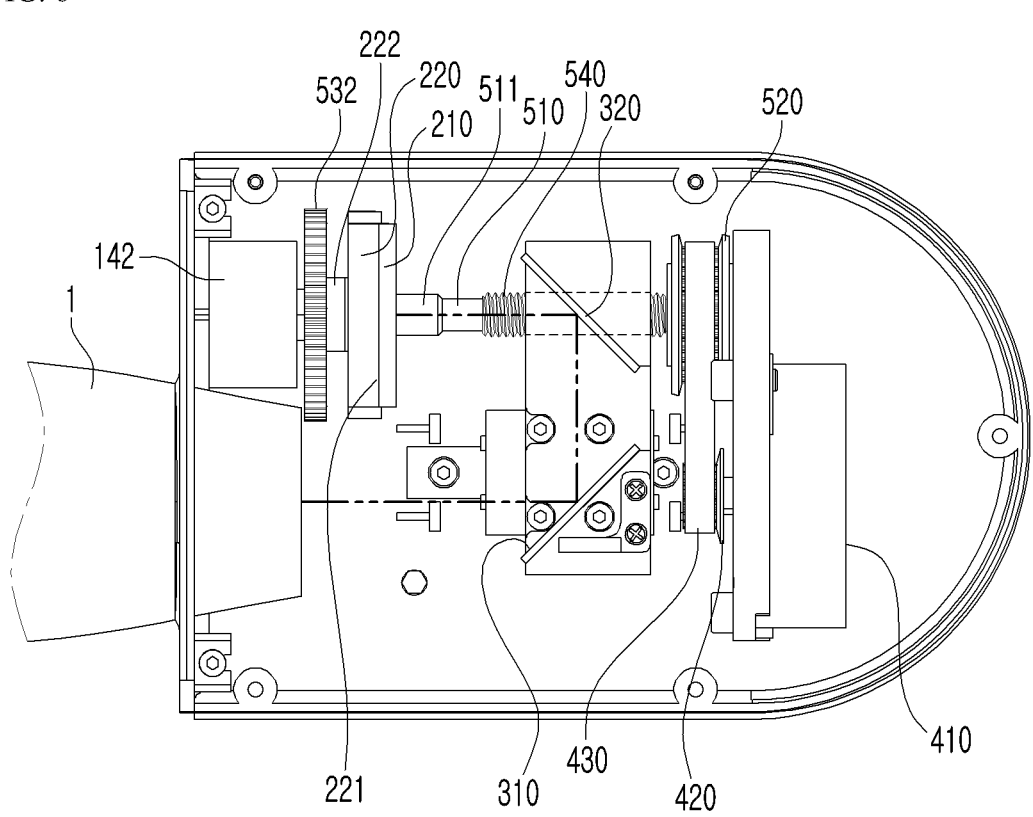

FIG. 1 is a perspective view of an oral scanner calibration device according to one embodiment of the present disclosure. FIGS. 2 and 3 are exploded perspective views of the oral scanner calibration device according to one embodiment of the present disclosure. FIG. 4 is a lateral cross-sectional view of the oral scanner calibration device according to one embodiment of the present disclosure. FIGS. 5 and 6 are cross-sectional views showing an operational process of the oral scanner calibration device according to one embodiment of the present disclosure.

As shown in FIGS. 1 to 3, an oral scanner calibration device 1000 according to one embodiment of the present disclosure is a device for calibrating an optical device of an oral scanner and includes a housing 100, a pattern plate part 200, and a reflector part 300.

The housing 100 according to one embodiment of the present disclosure forms an outer peripheral surface of the oral scanner calibration device 1000 and includes a body 110 forming an inner space, an insertion part 120 formed at one side of a front of the body 110 and into which an oral scanner body 1 is inserted to be supported, and a first cover 130 and a second cover 140 formed to cover the top and bottom of the body 110. A first support part 141 and a second support part 142 that may axially support a driving part 400 and a rotating part 500 which will be described below are positioned at the second cover 140 of the housing 100.

Generally, an oral scanner includes the oral scanner body 1 having an optical device and an imaging board disposed thereon and a probe tip having a reflector disposed therein, and the optical device includes a light source configured to irradiate light toward an opening of the oral scanner body 1 along a central axis of the oral scanner body 1 and a pair of imaging devices configured to condense light introduced through the opening to the imaging board.

Here, since oral scanning of a patient is performed while the probe tip is inserted into the oral cavity of the patient, a reflective member may get damp due to moisture in the oral cavity of the patient, and thus, in the case in which calibration is performed while the probe tip is mounted, accuracy of calibration may be degraded. Only the oral scanner body 1 from which the probe tip is removed may be inserted into the housing 100.

According to one embodiment of the present disclosure, the insertion part 120 may be formed to correspond to the shape of an end of the oral scanner body 1 for the oral scanner body 1 to be firmly fixed to the insertion part 120.

Meanwhile, the pattern plate part 200 according to one embodiment of the present disclosure is for calibrating the oral scanner while positioned inside the housing 100 and includes a pattern plate 210 and a seating part 220.

Specifically, the pattern plate 210 may be formed in a square shape and may have various patterns formed thereon. For example, a pattern may be formed so that, in a grid pattern, light and shade are clearly distinguished between grids adjacent in up-down and left-right directions.

Meanwhile, an angle of inclination of the pattern plate 210 according to one embodiment of the present disclosure may be set to be 40° or more and less than 50° based on incident light. In the case in which the pattern plate 210 is disposed to be orthogonal to the incident light, there is a disadvantage that each of the patterns formed on the pattern plate 210 has the same depth information (or height information) for the same surface. Thus, the pattern plate 210 is designed to be disposed to be inclined at a predetermined angle relative to incident light to increase an effect of calibration.

To this end, a front of the seating part 220 on which pattern plate 210 is seated may be formed of an inclined surface 221 that forms an angle of inclination of 40° or more and less than 50° relative to an optical axis of incident light.

Meanwhile, as shown in FIG. 3, the seating part 220 according to one embodiment of the present disclosure may include an extension 222 extending to a rear of the inclined surface 221 along the optical axis of the incident light. The extension 222 is integrally coupled to a first rotating part 530 of the rotating part 500 which will be described below, and thus, the pattern plate part 200 rotates in conjunction with rotation of the rotating part 500.

Meanwhile, due to being positioned to be spaced a predetermined distance apart from the central axis of the oral scanner body 1, the pattern plate part 200 according to one embodiment of the present disclosure may face the optical device inside the oral scanner body 1 through the reflector part 300.

Specifically, in order to reflect light irradiated from the optical device of the oral scanner body 1 toward the pattern plate part 200, the reflector part 300 may include a plurality of reflectors 310 and 320 and a support part 330 configured to support the reflectors 310 and 320 for the reflectors 310 and 320 to be inclined relative to the oral scanner body 1.

More specifically, the support part 330 includes a first inclined surface 331 formed to be inclined at an angle of, for example, 45° relative to the central axis of the oral scanner body 1 and a second inclined surface 332 formed to be inclined at an angle of, for example, 45° relative to the optical axis of incident light incident on the pattern plate part 200. A first reflector 310 is disposed on the first inclined surface 331, and a second reflector 320 is disposed on the second inclined surface 332. That is, a plane including the first inclined surface 331 and a plane including the second inclined surface 332 may be disposed to be orthogonal to each other.

In this case, light irradiated from the optical device may be reflected 180° through the first reflector 310 and the second reflector 320 and incident on the pattern plate 210. Here, the reflectors may be formed as rectangular mirrors but are not limited thereto, and of course, mirrors of various other shapes may be applied.

Meanwhile, the reflector part 300 according to one embodiment of the present disclosure may include a guide part 340 to linearly move along a guide rail 143 in conjunction with rotation of the rotating part 500 which will be described below.

Specifically, the guide rail 143 is provided on an inner side surface of the second cover 140 and longitudinally extends in a direction parallel to the central axis of the oral scanner body 1. Further, the guide part 340 is positioned at one side of a lower end of the support part 330, and a guide groove 341 corresponding to the guide rail 143 is formed on a bottom surface of the guide part 340. Here, when the guide rail 143 is seated on the guide groove 341, as will be described below, the reflector part 300 may linearly move in the longitudinal direction of the guide rail 143 during rotation of the rotating part 500.

Meanwhile, as described above, in an oral scanner using a stereo vision method, an image of one point of an oral cavity is captured by two or more imaging devices to obtain two or more pieces of image data, and 3D distance information is obtained based on the two or more pieces of image data, and thus calibration is frequently required for the oral scanner in order to obtain accurate 3D model data. Here, when an image of the pattern plate part is obtained from various angles and depths, accuracy of calibration can be improved.

To this end, the oral scanner calibration device 1000 according to one embodiment of the present disclosure may further include the driving part 400 and the rotating part 500.

The driving part 400 according to one embodiment of the present disclosure provides a driving force to the rotating part 500 and may include a driving motor 410, a driving gear 420, and a driving belt 430. The driving motor 410 may be supported on the above-mentioned first support part 141 of the housing 100, and the driving gear 420 in the shape of a pulley and the driving belt 430 surrounding an outer circumferential surface of the driving gear 420 may be provided at an end of a driving shaft of the driving motor 410. Here, a driving method of the driving part 400 is not limited to the above-described belt driving method, and various other driving methods may be applied.

Meanwhile, the oral scanner calibration device 1000 according to one embodiment of the present disclosure may further include a controller configured to control the driving part 400. Here, power may be supplied to the driving part 400 and the controller using an external power source or a battery positioned inside the oral scanner calibration device 1000.

Meanwhile, the rotating part 500 according to one embodiment of the present disclosure receives a driving force from the driving part 400 and rotates in conjunction with the pattern plate part 200 and the reflector part 300 and may include a rotating shaft 510, a power transmitter 520, the first rotating part 530, and a second rotating part 540.

Specifically, the rotating shaft 510 is in the shape of a rod that extends in the direction parallel to the central axis of the oral scanner body 1, and both ends of the rotating shaft 510 may be axially supported by the first support part 141 and the second support part 142 of the housing 100 so that the rotating shaft 510 is rotatable. A bearing that facilitates rotation of the rotating shaft 510 may be provided inside the first support part 141 and the second support part 142 according to one embodiment of the present disclosure.

The power transmitter 520 configured to receive the driving force of the driving part 400 is positioned at one end of the rotating shaft 510 according to one embodiment of the present disclosure. The power transmitter 520 may be formed in the shape of a pulley for the driving belt 430 of the driving part 400 to be wound around the power transmitter 520, but the shape of the power transmitter 520 is not limited thereto, and gears of various other shapes may be applied according to the driving method of the driving part 400.

The first rotating part 530 may be positioned at the other end of the rotating shaft 510 according to one embodiment of the present disclosure. According to one embodiment of the present disclosure, the first rotating part 530 may include a plurality of gears. For example, as shown in FIG. 3, the first rotating part 530 may include a first gear 531 positioned at the other end of the rotating shaft 510 and a second gear 532 engaged with the first gear 531 at an upper side of the first gear 531. Here, the first gear 531 and the second gear 532 may be axially supported by the second support part 142. The first gear 531 and the second gear 532 may each be formed in the shape of a spur gear but are not limited thereto, and of course, gears of various other shapes may be applied.

According to one embodiment of the present disclosure, the second gear 532 may be engaged with the extension 222 of the pattern plate part 200. Thus, when the rotating shaft 510 rotates, the pattern plate part 200 rotates in place about the optical axis of incident light.

According to one embodiment of the present disclosure, the second rotating part 540 may be positioned at one side of the rotating shaft 510. For example, as shown in FIG. 4, the second rotating part 540 may include screw threads provided on an outer circumferential surface of the rotating shaft 510. The screw threads of the second rotating part 540 may be coupled to the support part 330 of the reflector part 300 so that the second rotating part 540 and the reflector part 300 are rotatable relative to each other.

Meanwhile, since the reflector part 300 may rotate along the rotating shaft 510 due to a frictional force acting between the second rotating part 540 and the support part 330 when the rotating shaft 510 rotates, the guide part 340 may be seated on the guide rail 143 formed on the second cover 140 of the housing 100. In this case, rotation of the guide part 340 is restricted due to the guide rail 143 being positioned within a radius of rotation of the guide part 340, and the guide part 340 linearly moves in the longitudinal direction of the guide rail 143.

That is, the reflector part 300 linearly moves relative to the oral scanner body 1 in conjunction with the rotation of the rotating part 500.

According to one embodiment of the present disclosure, a step part 511 protruding in a radial direction of the rotating shaft 510 may be formed at both ends of the second rotating part 540 to limit a range of linear movement of the pattern plate part 200.

Hereinafter, an operational process of the oral scanner calibration device 1000 according to one embodiment of the present disclosure will be described in detail with reference to FIGS. 5 and 6.

When a driving signal is transmitted to the driving part 400 by the controller, the driving motor 410 operates, the power transmitter 520 connected to the driving gear 420 rotates, and the rotating shaft 510 rotates. Then, when the first rotating part 530 rotates due to the rotation of the rotating shaft 510, the pattern plate part 200 engaged with the first rotating part 530 rotates in place. That is, the pattern plate part 200 rotates about the optical axis of incident light in conjunction with the rotation of the rotating part 500.

Simultaneously, the reflector part 300 linearly moves in the longitudinal direction of the guide rail 143. That is, the reflector part 300 linearly moves relative to the oral scanner body 1 in conjunction with the rotation of the rotating part 500.

In this way, in the oral scanner calibration device 1000 according to one embodiment of the present disclosure, in conjunction with the rotation of the rotating part 500, the pattern plate part 200 rotates in place about the optical axis of incident light and the reflector part 300 linearly moves relative to the oral scanner body 1. Accordingly, an image of the pattern plate part 200 can be obtained from various angles and depths during calibration, and thus, accuracy of calibration can be improved.

Further, in the oral scanner calibration device 1000 according to one embodiment of the present disclosure, since the rotating part 500 receives a driving force from the driving part 400, calibration can be performed even without manual operation by a user, and thus convenience in use can be improved, and the time taken for calibration can be reduced.

The above-given description of the present disclosure is only illustrative, and those of ordinary skill in the art to which the present disclosure pertains should understand that the present disclosure may be easily modified to other specific forms without changing the technical spirit or essential features of the present disclosure. Therefore, the embodiments described above should be understood as illustrative, instead of limiting, in all aspects. For example, each element described as a single type may be embodied in a distributed manner, and likewise, elements described as being distributed may be embodied in a combined form.

The scope of the present disclosure is shown by the claims below, and all changes or modifications derived from the meaning and scope of the claims and their equivalent concepts should be construed as falling within the scope of the present disclosure.

DESCRIPTION OF REFERENCE NUMERALS

1: oral scanner body
1000: oral scanner calibration device
100: housing, 110: body, 120: insertion part, 130: first cover, 140: second cover, 141: first support part, 142: second support part, 143: guide rail
200: pattern plate part, 210: pattern plate, 220: seating part, 221: inclined surface, 222: extension

300: reflector part, 310: first reflector, 320: second reflector, 330: support part, 331: first inclined surface, 332: second inclined surface, 340: guide part, 341: guide groove
400: driving part, 410: driving motor, 420: driving gear, 430: driving belt
500: rotating part, 510: rotating shaft, 511: step part, 520: power transmitter, 530: first rotating part, 531: first gear, 532: second gear, 540: second rotating part

The invention claimed is:

1. An oral scanner calibration device comprising:
a casing into which an oral scanner body is inserted;
a reflector part disposed on a central axis of the oral scanner body and configured to reflect light irradiated from an optical device of the oral scanner body;
a pattern plate part configured to face the optical device through the reflector part;
a rotating part mechanically fastened to the reflector part and the pattern plate part; and
a driving part configured to provide a driving force to the rotating part,
wherein, in conjunction with rotation of the rotating part, the reflector part linearly moves relative to the oral scanner body, and the pattern plate part rotates about an optical axis of the light reflected by the reflector part,
wherein the rotating part includes:
a rotating shaft configured to be rotated by the driving part and extend in a longitudinal direction;
a first rotating part positioned at the other end of the rotating shaft and configured to transmit the driving force to the pattern plate part; and
a second rotating part positioned at one side of the rotating shaft and configured to transmit the driving force to the reflector part.

2. The oral scanner calibration device of claim 1, wherein the pattern plate part includes:
a pattern plate; and
a support part configured to be engaged with the first rotating part and support the pattern plate for the pattern plate to be inclined relative to the optical axis.

3. The oral scanner calibration device of claim 1, wherein the reflector part includes:
a plurality of reflectors; and
a support part configured to be rotatably coupled to the second rotating part and support the reflectors,
wherein the support part linearly moves during rotation of the second rotating part.

4. The oral scanner calibration device of claim 3, wherein:
the reflectors consist of a first reflector and a second reflector;
the first reflector is positioned to form a 45° angle with the central axis;
the second reflector is positioned to form a 45° angle with the optical axis; and
a plane including the first reflector and a plane including the second reflector are orthogonal to each other.

5. The oral scanner calibration device of claim 4, wherein:
the reflector part is seated on a guide rail formed on the housing; and
the rotating shaft and the support part are mechanically fastened so that, during rotation of the rotating shaft, the reflector part linearly moves along the guide rail.

* * * * *